United States Patent
Hadley et al.

(10) Patent No.: US 9,757,134 B2
(45) Date of Patent: Sep. 12, 2017

(54) SYSTEM FOR DELIVERY AND DEPLOYMENT OF AN OCCLUDER AND METHOD

(71) Applicant: Cook Medical Technologies LLC, Bloomington, IN (US)

(72) Inventors: Rick Hadley, Otterbein, IN (US); Kevin Wilger, Lafayette, IN (US); Ryan Bradway, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 229 days.

(21) Appl. No.: 14/723,568

(22) Filed: May 28, 2015

(65) Prior Publication Data

US 2015/0359539 A1   Dec. 17, 2015

Related U.S. Application Data

(60) Provisional application No. 62/011,085, filed on Jun. 12, 2014.

(51) Int. Cl.

| | | |
|---|---|---|
| *A61M 29/00* | (2006.01) | |
| *A61B 17/12* | (2006.01) | |
| *A61B 17/00* | (2006.01) | |
| *A61B 90/00* | (2016.01) | |

(52) U.S. Cl.
CPC .. *A61B 17/12031* (2013.01); *A61B 17/12109* (2013.01); *A61B 17/12172* (2013.01); *A61B 2017/00292* (2013.01); *A61B 2017/00455* (2013.01); *A61B 2017/1205* (2013.01); *A61B 2017/12054* (2013.01); *A61B 2090/038* (2016.02); *A61B 2218/002* (2013.01)

(58) Field of Classification Search
CPC ............ A61B 17/12; A61B 17/1205; A61B 17/12031; A61B 17/12172; A61B 17/12022; A61B 2017/1205; A61B 2017/12054; A61B 2017/00367; A61M 29/00

See application file for complete search history.

(56) References Cited

U.S. PATENT DOCUMENTS

| | | | |
|---|---|---|---|
| 4,440,170 A * | 4/1984 | Golden | A61B 17/128 606/142 |
| 6,669,713 B2 * | 12/2003 | Adams | A61B 17/0643 606/153 |
| 8,202,246 B2 | 6/2012 | Kugler et al. | |
| 8,382,813 B2 | 2/2013 | Shumer | |
| 8,551,135 B2 | 10/2013 | Kladakis et al. | |
| 2013/0046373 A1 | 2/2013 | Cartledge et al. | |

* cited by examiner

*Primary Examiner* — Victor Nguyen
(74) *Attorney, Agent, or Firm* — Liell & McNeil

(57) ABSTRACT

A system for delivery and deployment of an occluder includes a handle, an actuating mechanism with a motion amplifier and a sheath positioning mechanism within the handle. A driveshaft of the actuating mechanism extends through the handle, the sheath positioning mechanism, and an attached sheath so as to couple with an occluder deployed via the driveshaft within a body lumen in a patient.

13 Claims, 5 Drawing Sheets

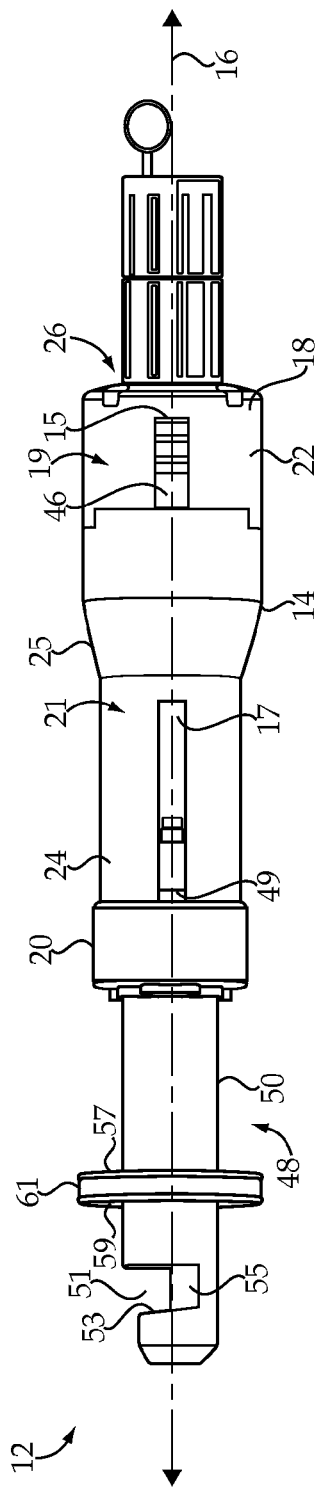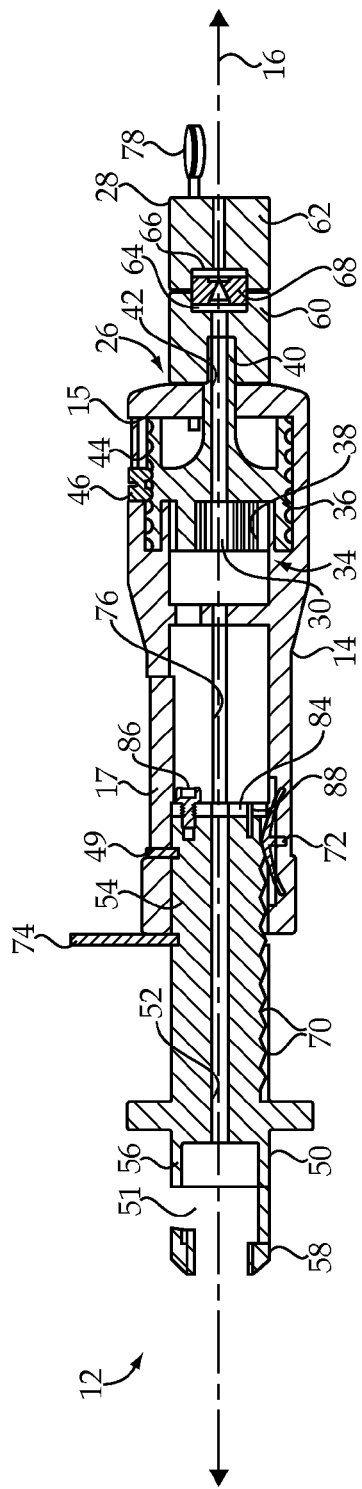

SYSTEM FOR DELIVERY AND DEPLOYMENT OF AN OCCLUDER AND METHOD

TECHNICAL FIELD

The present disclosure relates generally to delivery and deployment of an occluder device, and more particularly to a control handle assembly with a motion amplifying actuating mechanism and sheath positioning mechanism for delivery and deployment of an occluder.

BACKGROUND

A wide variety of different devices have been proposed for occluding body lumens and openings between body lumens in patients over the years. It is common for devices delivered intraluminally to be initially introduced in a low profile state, and upon reaching a target location adjusted to a deployed state. In the case of occlusion devices intended to limit or block flow of body fluid through a lumen, by necessity the device is delivered in a form not completely occluding the lumen, and then transitioned to a form where greater or total occlusion occurs or can commence. Various factors relating to this need to substantially change shape or size present challenges to successful design and exploitation of such devices.

Occlusion devices generally fall into two classes. Certain occlusion devices are self-expanding, relying upon internal spring biasing of the device to enable expanding once a restrictive force is relieved. Another class of occlusion devices rely upon a mechanism for driving expansion. Self-expanding devices of course offer the advantage of simplicity in delivery and deployment. Driven devices can be more complicated to deploy, but can have the advantage of greater control over deployment, and potentially improved prospects for relatively simple and straightforward recapture by reversing operation of an integral driven expander. Known devices and delivery systems have shown great promise, but there remains ample room for improvement.

SUMMARY OF THE DISCLOSURE

In one aspect, a system for delivery and deployment of an occluder includes a handle defining a longitudinal axis extending between a proximal handle end and a distal handle end, and an actuating mechanism including a driver and a rotatable driven unit within the handle. The actuating mechanism further includes a motion amplifier operably coupled between the driver and the driven unit, and a driveshaft coupled to the driven unit and fixed to rotate therewith. The system further includes a sheath positioning mechanism including a tubular insert positioned partially within the handle at a location distal to the actuating mechanism. A sheath is coupled to the tubular insert, and extends in a distal direction from the handle. The driveshaft extends through the handle, the tubular insert, and the sheath, and is held via the coupling to the driven unit at a fixed axial position within the handle. The tubular insert is movable within the handle between an advanced position further from the driven unit, and a retracted position closer to the driven unit, such that retracting the tubular insert pulls back the sheath about an assembly of the driveshaft and an occluder so as to expose the occluder for deployment via the driveshaft within a body lumen in a patient.

In another aspect, a control handle assembly for delivering and deploying an occluder includes a handle defining a longitudinal axis extending between a proximal handle end and a distal handle end, and an actuating mechanism including a driver and a rotatable driven unit within the handle for coupling with a driveshaft so as to rotate the driveshaft at a fixed axial position within the handle, and a motion amplifier operably coupled between the driver and the driven unit. The assembly further includes a sheath positioning mechanism including a tubular insert positioned partially within the handle at a location distal to the actuating mechanism. The tubular insert defines a through-bore oriented to receive the driveshaft and extending between a proximal insert end positioned within the handle and a distal insert end. The distal insert end includes a sheath-coupling tip for attaching a sheath positionable about the driveshaft. The tubular insert is movable within the handle between an advanced position where the sheath-coupling tip is at a greater axial distance from the driven unit, and a retracted position where the sheath-coupling tip is at a lesser axial distance from the driven unit, such that retracting the tubular insert pulls back an attached sheath about an assembly of the driveshaft and an occluder to expose the occluder for deployment via the driveshaft within a body lumen in a patient.

In still another aspect, a method of deploying an occluder at a target location includes retracting a tubular insert into a handle so as to pull an attached sheath toward the handle, and operating an actuating mechanism within the handle so as to rotate a driveshaft extending through the handle, the tubular insert, and the sheath. The driveshaft is coupled to an occluder exposed for deployment via the pulling of the sheath. The method further includes gripping a body of the occluder via the sheath so as to limit rotation of the body during the rotating of the driveshaft, and expanding the body of the occluder to a deployed state via an expander in the occluder driven via the rotation of the driveshaft. The method still further includes decoupling the occluder from the driveshaft and sheath.

BRIEF DESCRIPTION OF THE DRAWINGS

FIG. 1 is a side diagrammatic view of a control handle assembly, according to one embodiment;

FIG. 2 is a sectioned side diagrammatic view of the assembly of FIG. 1;

DETAILED DESCRIPTION

Figure 3:
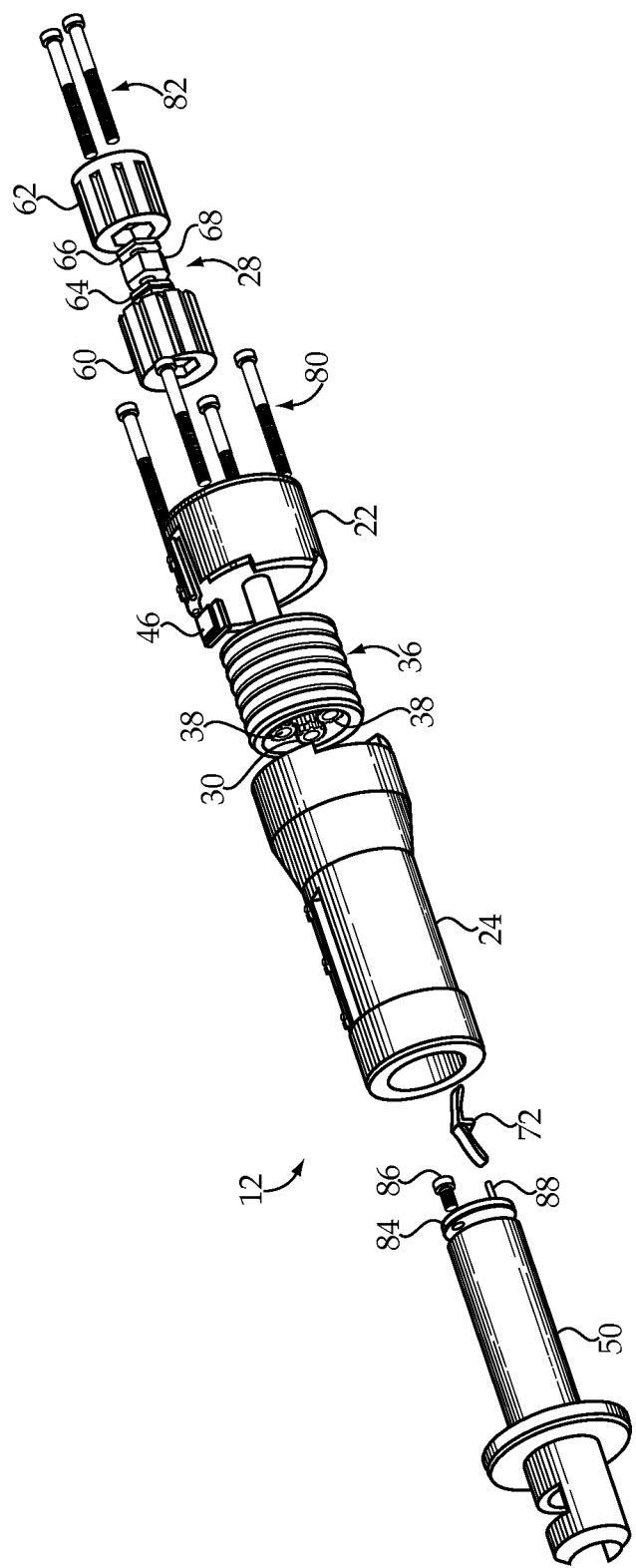
FIG. 3 is an exploded view, in perspective, of the assembly of FIGS. 1 and 2.

Referring to FIG. 1, there is shown a control handle assembly 12 for delivering and deploying an occluder device, according to one embodiment. Control handle assembly 12 is adapted for use with self-expanding and driven occluder devices, such as mesh occluders. It is contemplated that a principal application of control handle assembly 12 will be with driven mesh occluders, as further described herein, although the present disclosure is not limited as such. Assembly 12 may include an elongate handle 14 defining a longitudinal axis 16 extending between a proximal handle end 18 and a distal handle end 20. An actuating mechanism 26 is coupled with and positioned partially within handle 14. A sheath positioning mechanism 48 is also coupled with and positioned partially within handle 14. Handle 14 may include a proximal handle piece 22, a distal handle piece 24, and a taper 25 formed integrally with one of pieces 22 and 24 to render the general shape adapted for manual grasping as depicted in FIG. 1.

In the illustrated embodiment, handle 14 has a first longitudinal slot 15 formed therein, and located at least predominantly in proximal handle piece 22. A second longitudinal slot 17 is also formed in handle 14, at least predominantly in piece 24. First slot 15 is adjacent proximal handle end 18, whereas second slot 17 is adjacent distal handle end 20. A principal function of actuating mechanism 26 will be actuation of an expander in an occluder to be deployed via control handle assembly 12. A principal function of sheath positioning mechanism 48 will be the positioning of a sheath relative to a driveshaft driven via actuating mechanism 26 and an occluder forming an assembly with the driveshaft. Example features and operating principles of the various components of control handle assembly 12 will be further apparent by way of the following description.

Sheath positioning mechanism 48 includes a tubular insert 50 positioned partially within handle 14 at a location distal to actuating mechanism 26. In FIG. 1, a sheath position indicator 49 is visible positioned within slot 17. Indicator 49 is coupled with tubular insert 50 so as to slide in axial directions within slot 17 in response to moving tubular insert 50 between an advanced position and a retracted position, as further discussed herein. Indicia 21 of sheath position, including for instance markings, indentations, or appliqués such as stickers, are visible to one side of slot 17. As further discussed herein, sliding indicator 49 as tubular insert 50 moves enables a clinician to visually monitor at least approximate relative sheath position even where the sheath is not visible because of its placement within a body lumen in a patient, the significance of which will be apparent from the following description. Additional indicia 17 are shown to one side of slot 15 and serve similar functions in connection with an occluder release indicator 19 within slot 15.

Referring also now to FIG. 2, in a practical implementation strategy actuating mechanism 26 includes a driver 28, a rotatable driven unit 30 within handle 14 for coupling with a driveshaft so as to rotate the driveshaft at a fixed axial position within handle 14, and a motion amplifier 34 operably coupled between driver 28 and driven unit 30. In one embodiment, motion amplifier 34 includes a hub 36 and one or more planet gears 38 in a planetary gear assembly within handle 14. Driven unit 30 may include a sun gear in the planetary gear assembly. Driver 28 may include a knob 60 fixed to rotate with hub 36, in other words rotating to drive rotation of hub 36. In a practical implementation strategy, knob 60, hub 36 and sun gear 30 may each be rotatable about longitudinal axis 16. In other embodiments, a thumb wheel, trigger or still another mechanical contrivance could be used as a driver, and rotatable about an axis of rotation transverse or parallel to axis 16. A second knob 62 may be coupled to knob 60 in a practical implementation strategy, with a hemostasis seal trapped between knobs 60 and 62. In a further practical implementation strategy, the hemostasis seal may be comprised of a first sealing element 64, a second sealing element 66, and a third sealing element 68 having an internally tapered shape, sandwiched between sealing elements 64 and 66. Sealing elements 64 and 66 may be silicone seals, pierced via a wire guide or driveshaft passed through knobs 60 and 62, through a lumen 42 extending through hub 36, and also through sun gear 30 as further discussed herein.

In the illustrated embodiment, knob 60 is mounted upon a stem 40 of hub 36 that protrudes out of handle 14. In other embodiments, the relationship might be reversed, such that knob 60 has a stem that extends into handle 14, or some other arrangement altogether might be used. A pin 78 may extend all the way through knobs 60 and 62 and into handle 14, so as to restrict rotation of driver 28 until such time as it is desirable to operate actuating mechanism 26. A motion amplification ratio between driver 28 and driven unit 30 may be about four to one in certain embodiments, but could be more or less. Also visible in FIG. 2 is an external thread 44 on hub 36. As noted above, occluder release indicator 46 is slidable within slot 15. In the illustrated embodiment, indicator 46 is in contact with external thread 44 so as to slide in axial directions within slot 15 in response to rotation of hub 36.

Also shown in FIG. 2 are additional features of sheath positioning mechanism 48, including a through-bore 52 defined by tubular insert 50 and oriented to receive a driveshaft coupled with driven unit 30. Through-bore 52 extends between a proximal insert end 54 positioned within handle 14, and a distal insert end 56 positioned without handle 14. Distal insert end 56 includes a sheath-coupling tip 58 for attaching a sheath positionable about the driveshaft to be coupled to driven unit 30. Tubular insert 50 is movable within handle 14 between an advanced position where insert 50 and in particular sheath coupling tip 58 is positioned further from and at a greater axial distance from driven unit 30, and a retracted position. It will be recalled that a driveshaft coupled with driven unit 30 may be coupled so that it occupies a fixed axial position within handle 14. At the retracted position of tubular insert 50, tip 58 is at a lesser axial distance from driven unit 30, such that retracting insert 50 pulls back an attached sheath about an assembly of the driveshaft and an occluder to expose the occluder for deployment via the driveshaft within a body lumen in a patient. For coupling with a sheath, tip 58 includes a notch 51. Notch 51 may be formed in part by a first surface 53 oriented in a proximal direction, and in part by a second surface 55 oriented normal or otherwise transverse to first surface 53.

From the present description and illustration it will be appreciated that coupling a sheath, typically in a sheath assembly, to tip 58 can bring the sheath assembly to bear against surface 53 when an axial pulling force is applied by retracting tubular insert 50, causing the sheath to be pulled back. Surface 55, or another suitably oriented and located surface can be brought to bear against a part of the sheath assembly so that rotation of the sheath assembly is prevented during delivery and deployment of an occluder, except where a clinician desires to rotate the sheath and sheath assembly by rotating the overall system that also includes assembly 12. Other notch configurations, and other contrivances such as a clamping mechanism, threads, clips or the like could be used to couple sheath positioning mechanism 48 with a sheath. To enable moving tubular insert 50 between its advanced and retracted positions, tubular insert 50 may also include a radially projecting positioning flange 61 positioned proximal of notch 51, for manually moving tubular insert 50 between the advanced and retracted positions. In a practical implementation strategy, flange 54 includes a proximally oriented surface 57 and an opposite distally oriented surface 59, enabling a clinician to pull tubular insert 50 into handle 14 or push tubular insert 50 out of handle 14. A clip 74 may be positioned about tubular insert 50 in a practical implementation strategy, and prevents tubular insert 50 from being inadvertently refracted into handle 14. When it is desirable to use assembly 12, clip 74 may be removed. Tubular insert 50 may also include one or more grooves 70 which are generally oriented so as to be at least partially circumferential of axis 16. Clip 74 may be shaped so as to elastically deform about tubular insert 50, and selectively engage within any one of grooves 70. Clip 74 could thus be used to lock tubular insert 50 at any of a plurality of axial positions relative to handle 14. Assembly 12 may still further include a detent 72 seated within one of grooves 70, and positionable via deformation occurring in response to sliding tubular insert 50 between its advanced and retracted positions to reseat in any other one of the plurality of grooves.

Referring also now to FIG. 3, there is shown an exploded view of assembly 12, illustrating a limiting ring or disc 84 configured to couple with tubular insert 50, as shown in FIG. 2. A fastener 86 passes through limiting disc 84 and is received within tubular insert 50. A pin 88 or the like also passes through limiting disc 84 and is received within tubular insert 50. Limiting disc 84 can assist in orienting parts of assembly 12 for assembly, and prevent decoupling sheath positioning mechanism 48 from handle 14 by serving as a stop that contacts detent 72. In one embodiment, limiting disc 84 could include a radial projection received in a groove 76 formed in handle 14, and illustrated in FIG. 2. Also shown in FIG. 3 are a plurality of fasteners 80 which pass through handle piece 22 and into handle piece 24 to capture the planetary gear assembly comprised of hub 36, planet gears 38 and sun gear 30 and rotatably journal the same. Another set of fasteners 82 pass through knob 62 and into knob 60 to attach knobs 62 and 60 together and sandwich sealing elements 64, 66 and 68 between knobs 62 and 60.

Figure 4:
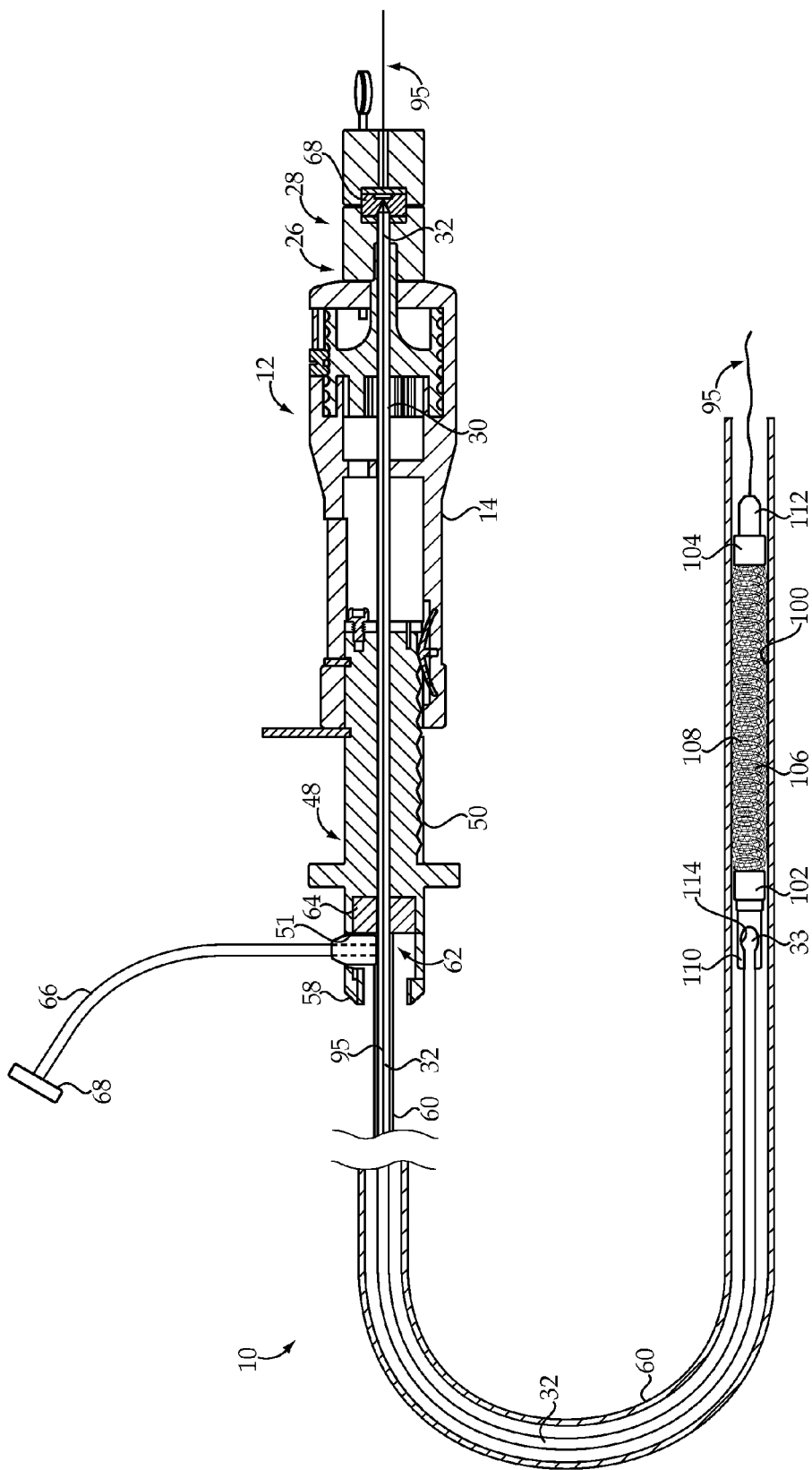
FIG. 4 is a sectioned side diagrammatic view of a system including the control handle assembly of FIGS. 1-3.

Referring also now to FIG. 4, there is shown control handle assembly 12 coupled with other components to form a system 10 for delivery and deployment of an occluder. System 10 includes handle 14 and the other components of assembly 12 described above. System 10 also includes a driveshaft 32 coupled to driven unit 30 in actuating mechanism 26 such that driveshaft 32 is fixed to rotate with driven unit 30. In a practical implementation strategy, driveshaft 32 may have the form of an elongate hollow flexible cannula defining a longitudinally extending central lumen 90. An outer surface of driveshaft 32 may have a polygonal or otherwise non-circular shape at a suitable location such that upon passing through driven unit 30, driveshaft 32 is rotatably fixed to driven unit 30 via engagement with mating surfaces therein. Driveshaft 32 may also be passed in a distal to proximal direction through handle 14 and other components of assembly 12 up until a point at which driveshaft 32 contacts element 68. Rotating driver 28 will thus tend to impart amplified rotation to driveshaft 32.

A sheath 60, part of a sheath assembly 62, is shown coupled to tip 58 of tubular insert 50 and extends in a distal direction from handle 14. Sheath assembly 62 also includes a hub 64 received within tip 58 via positioning in notch 51. A side tube 66 is coupled to sheath 60, and may include a fitting 68 or the like for fluidly connecting to a source of fluid to be injected through sheath 60 into a body lumen in a patient. It will therefore be understood that sheath 60 may have a port connecting to tube 66. Driveshaft 32 extends through handle 14, tubular insert 50, and sheath 60. A distal tip 33 of driveshaft 32 is coupled with an occluder 100 such that occluder 100 forms an assembly with driveshaft 32, positioned within sheath 60.

In the illustrated embodiment, occluder 100 includes a driven occluder having a mesh body 106 extending between a proximal hub 102 and a distal hub 104 having a distal tip 112. A proximal tip 110 is rotatable relative hub 102, and distal tip 112 is profiled so as to be atraumatic. An expander 108 extends through mesh body 106 and is coupled with each of tips 110 and 112. In a practical implementation strategy, expander 108 may include two coil pieces, each fixed to one of tips 110 and 112, and overlapping such that relative rotation between the coil pieces causes them to helically engage one another and shorten or increase a distance between hubs 102 and 104. A wire guide 95 extends all the way through other components of system 10, including driver 28, handle 14, tubular insert 50, sheath 60 and occluder 100, within lumen 90 of driveshaft 32.

INDUSTRIAL APPLICABILITY

Figure 5:
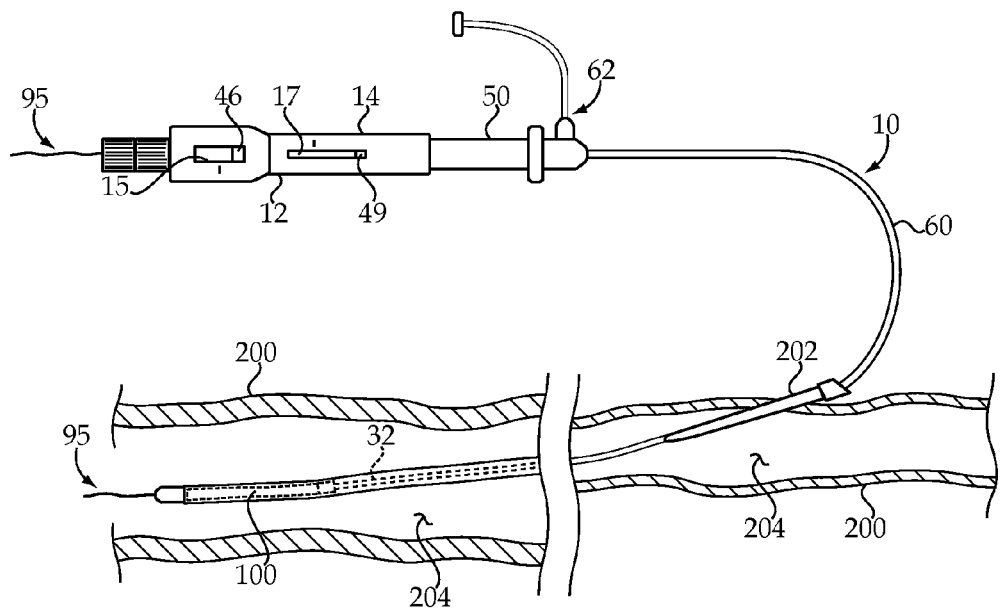
FIG. 5 is a diagrammatic view at one stage of a procedure, according to one embodiment.

Referring also now to FIG. 5, there is shown system 10 as it might appear having been advanced over wire guide 95 to position part of sheath 60 within a body lumen 204 in a body structure 200 such as a vein or artery in a patient. An introducer 202 is shown as it might appear providing an entry pathway through the patient's skin into lumen 204. Occluder 100 has been thusly advanced to a target location within the body lumen of the patient. It can be seen from FIG. 5 that tubular insert 50 is at an advanced position, and indicator 49 is positioned at a distal end of slot 17. Indicator 46 is positioned at a distal end of slot 15.

Figure 6:
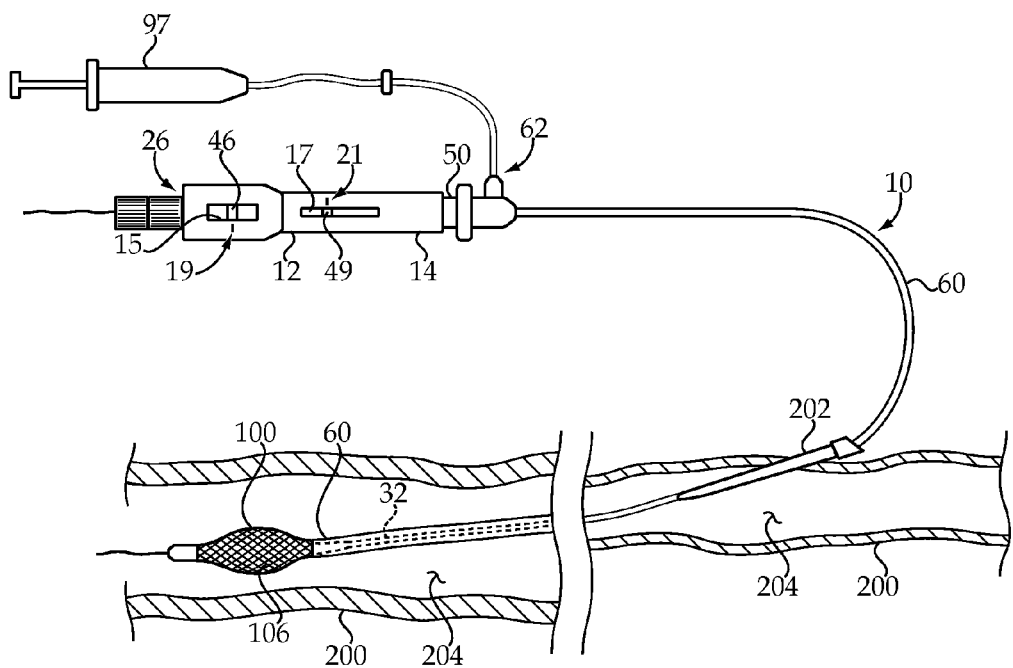
FIG. 6 is a diagrammatic view at another stage of the procedure.

Referring also now to FIG. 6, there is shown system 10 as it might appear where tubular insert 50 has been retracted part-way from its advanced position to its retracted position, and indicator 49 is approximately adjacent to indicia 21. A syringe 97 is coupled with sheath assembly 62 to enable a clinician to selectively inject fluid, such as contrast agent, so as to visualize progress in expanding occluder 100. It can further be seen that retracting tubular insert 50 into handle 14 has pulled sheath 60 toward handle 14, so as to expose most of occluder 100 within body lumen 204. Actuating mechanism 26 has been operated so as to rotate driveshaft 32, causing indicator 46 to slide within slot 15 approximately to align with indicia 19. In one practical implementation strategy, tubular insert 50 may be retracted approximately to the point where indicator 49 aligns with indicia 21, to present a state where sheath 60 extends just slightly over mesh body 106 of occluder 100. At this state, sheath 60 may be in contact with mesh body 106, gripping the same via frictional interaction so as to limit rotation of body 106 during rotating of driveshaft 32. Those skilled in the art will appreciate that this strategy of gripping body 106 enables expander 108 to be driven relative to body 106, instead of rotating the entire occluder 100 within the body lumen.

Figure 7:
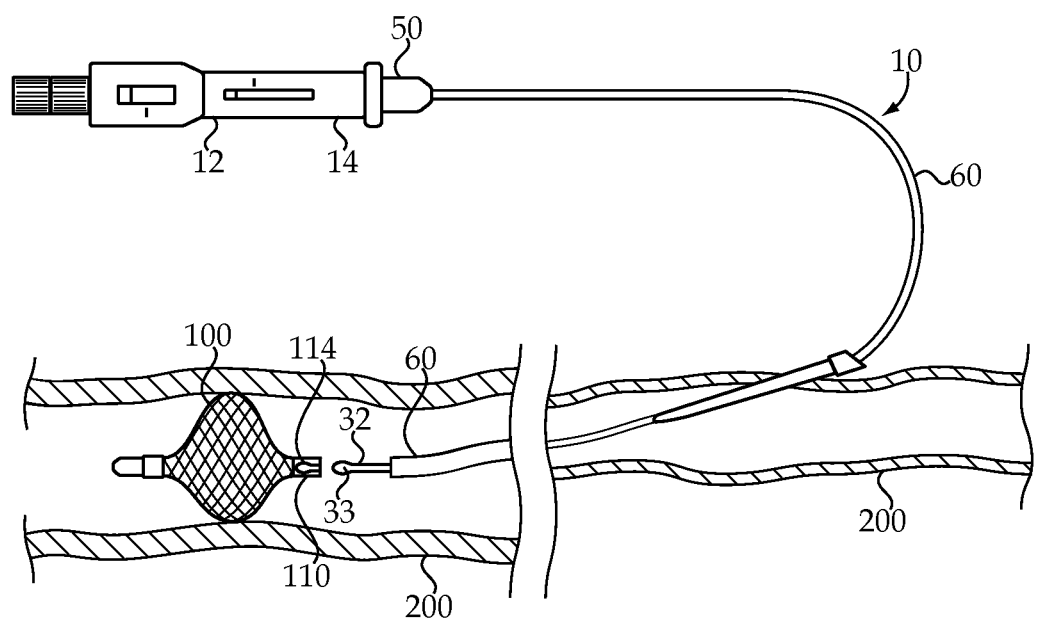
FIG. 7 is a diagrammatic view at yet another stage of the procedure.

Referring now to FIG. 7, there is shown system 10 as it might appear where body 106 of occluder 100 has been expanded to a deployed state via expander 108 as driven via the rotation of driveshaft 32. In FIG. 7, occluder 100 has been decoupled from driveshaft 32 and sheath 60. A shaped distal tip 33 of driveshaft 32 has been withdrawn from a complementarily shaped slot 114 in tip 110 of occluder 100. At this stage, occluder 100 can be considered fully deployed for service, and the other components of system 10 withdrawn from the patient.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A system for delivery and deployment of an occluder comprising:
a handle defining a longitudinal axis extending between a proximal handle end and a distal handle end;
an actuating mechanism including a driver, a rotatable driven unit within the handle, a motion amplifier operably coupled between the driver and the driven unit, and a driveshaft coupled to the driven unit and fixed to rotate therewith;
a sheath positioning mechanism including a tubular insert positioned partially within the handle at a location distal to the actuating mechanism;
a sheath coupled to the tubular insert, and extending in a distal direction from the handle;
the driveshaft extending through the handle, the tubular insert, and the sheath, and being held via the coupling to the driven unit at a fixed axial position within the handle; and
the tubular insert being movable within the handle between an advanced position further from the driven unit, and a retracted position closer to the driven unit, such that retracting the tubular insert pulls back the sheath about an assembly of the driveshaft and an occluder so as to expose the occluder for deployment via the driveshaft within a body lumen in a patient.

2. The system of claim 1 wherein the driveshaft defines a wire guide lumen.

3. The system of claim 2 wherein the driver includes a knob positioned to rotate about the longitudinal axis.

4. The system of claim 3 wherein the driver includes a second knob adjacent the first knob, and the system further comprises a hemostasis seal trapped between the first and second knobs.

5. The system of claim 2 wherein the actuating mechanism includes a planetary gear assembly.

6. The system of claim 5 wherein the motion amplifier includes a hub and a planet gear in the planetary gear assembly, and wherein the driven unit includes a sun gear in the planetary gear assembly.

7. The system of claim 6 wherein the hub includes an external thread.

8. The system of claim 7 wherein the handle has a longitudinal slot formed therein, and further comprising an occluder release indicator within the slot and in contact with the external thread so as to slide in axial directions within the slot in response to rotation of the hub.

9. The system of claim 2 wherein the tubular insert includes a radially projecting positioning flange for manually moving the tubular insert between the advanced and retracted positions.

10. The system of claim 9 wherein the handle has a longitudinal slot formed therein, and further comprising a position indicator within the slot and coupled with the tubular insert so as to slide in axial directions within the slot in response to moving the tubular insert between the advanced and retracted positions.

11. The system of claim 2 wherein the tubular insert has a plurality of grooves formed therein and each being at least partially circumferential of the tubular insert, and further comprising a detent seated within one of the plurality of grooves and positionable via sliding the tubular insert between the advanced and retracted positions to reseat in any one of the plurality of grooves.

12. A method of deploying an occluder at a target location with a system that includes a handle defining a longitudinal axis extending between a proximal handle end and a distal handle end; an actuating mechanism including a driver, a rotatable driven unit within the handle, a motion amplifier operably coupled between the driver and the driven unit, and a driveshaft coupled to the driven unit and fixed to rotate therewith; a sheath positioning mechanism including a tubular insert positioned partially within the handle at a location distal to the actuating mechanism; a sheath coupled to the tubular insert, and extending in a distal direction from the handle; the driveshaft extending through the handle, the tubular insert, and the sheath, and being held via the coupling to the driven unit at a fixed axial position within the handle; and the tubular insert being movable within the handle between an advanced position further from the driven unit, and a retracted position closer to the driven unit, such that retracting the tubular insert pulls back the sheath about an assembly of the driveshaft and an occluder so as to expose the occluder for deployment via the driveshaft within a body lumen in a patient, the method comprising the steps of:
retracting the tubular insert into the handle so as to pull the attached sheath toward the handle;
operating the actuating mechanism within the handle so as to rotate the driveshaft extending through the handle, the tubular insert, and the sheath, and coupled to the occluder exposed for deployment via the pulling of the sheath;
gripping a body of the occluder via the sheath so as to limit rotation of the body during the rotating of the driveshaft;
expanding the body of the occluder to a deployed state via an expander in the occluder driven via the rotation of the driveshaft; and
decoupling the occluder from the driveshaft and sheath.

13. The method of claim 12 further comprising a step of sliding a sheath position indicator within a groove in the handle responsive to the retracting of the tubular insert, and sliding an occluder release indicator within another groove in the handle responsive to the operating of the actuating mechanism.

* * * * *